United States Patent
Frangioni et al.

(10) Patent No.: US 7,288,759 B2
(45) Date of Patent: Oct. 30, 2007

(54) TISSUE-LIKE PHANTOMS

(75) Inventors: John V. Frangioni, Wayland, MA (US);
Alec M. De Grand, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 224 days.

(21) Appl. No.: 11/222,949

(22) Filed: Sep. 9, 2005

(65) Prior Publication Data

US 2006/0056580 A1 Mar. 16, 2006

Related U.S. Application Data (60) Provisional application No. 60/608,200, filed on Sep. 9, 2004.

(51) Int. Cl.
*G01N 23/00* (2006.01)
*G01D 18/00* (2006.01)

(52) U.S. Cl. .................. 250/252.1; 250/505.1; 250/506.1; 378/18; 378/207; 600/476; 600/478; 600/312; 382/131

(58) Field of Classification Search .............. None
See application file for complete search history.

(56) References Cited

U.S. PATENT DOCUMENTS

2005/0145786 A1* 7/2005 Rice et al. ............... 250/252.1

OTHER PUBLICATIONS

Boehm et al., "Contrast-enhanced near-infrared laser mammography with a prototype breast scanner: feasibility study with tissue phantoms and preliminary results of imaging experimental tumors," Invest. Radiol., 36:573-81 (2001).
Cheong et al., "A review of the optical properties of biological tissues," IEEE J. Quantum Electronics, 26:2166-2185 (1990).
Cubeddu et al., "A solid tissue phantom for photon migration studies," Phys. Med. Biol., 42:1971-9 (1997).
De Grand and Frangioni, "An operational near-infrared fluorescence imaging system prototype for large animal surgery," Technol. Cancer Res. Treat., 2:553-562 (2003).
De Grand et al., "Tissue-like phantoms for near-infrared fluorescence imaging system assessment and the training of surgeons," J. Biomed. Opt., 11:014007 (2006).
English et al., "Sub-millimeter technetium-99m calibration sources," Mol. Imag. Biol., 4: 380-384 (2002).
Frangioni, "In vivo near-infrared fluorescence imaging," Curr. Opin. Chem. Biol., 7:626-634 (2003).

(Continued)

*Primary Examiner*—Nikita Wells
*Assistant Examiner*—Zia R. Hashmi
(74) *Attorney, Agent, or Firm*—Fish & Richardson P.C.

(57) ABSTRACT

The invention is based, in part, on the discovery that by combining certain components one can generate a tissue-like phantom that mimics any desired tissue, is simple and inexpensive to prepare, and is stable over many weeks or months. In addition, new multi-modal imaging objects (e.g., beads) can be inserted into the phantoms to mimic tissue pathologies, such as cancer, or merely to serve as calibration standards. These objects can be imaged using one, two, or more (e.g., four) different imaging modalities (e.g., x-ray computed tomography (CT), positron emission tomography (PET), single photon emission computed tomography (SPECT), and near-infrared (NIR) fluorescence) simultaneously.

19 Claims, 6 Drawing Sheets

OTHER PUBLICATIONS

Giller et al., "Validation of a near-infrared probe for detection of thin intracranial white matter structures," J. Neurosurg., 98:1299-306 (2003).

Jiang et al., "Quantitative analysis of near-infrared tomography: sensitivity to the tissue-simulating precalibration phantom," J. Biomed. Opt., 8: 308-15 (2003).

Kelly et al., "Optical CT reconstruction of 3D dose distributions using the ferrous-benzoic-xylenol (FBX) gel dosimeter," Med. Phys., 25:1741-50 (1998).

Ma et al., "Determination of complex refractive index of polystyrene microspheres from 370 to 1610 nm," Phys. Med. Biol., 48: 4165-72 (2003).

Prahl et al., "Determining the optical properties of turbid media by using the adding-doubling method," Appl. Opt., 32: 559-568 (1993).

Quan et al., "Glucose determination by a pulsed photoacoustic technique: an experimental study using a gelatin-based tissue phantom," Phys. Med. Biol., 38:1911-22 (1993).

Wagnieres et al., "An optical phantom with tissue-like properties in the visible for use in PDT and fluorescence spectroscopy," Phys. Med. Biol., 42:1415-26 (1997).

Zaheer et al., "In vivo near-infrared fluorescence imaging of osteoblastic activity," Nat. Biotechnol., 19: 1148-1154 (2001).

* cited by examiner

FIG. 2A Gelatin (no dilution)
FIG. 2B Intralipid (1:100)
FIG. 2C Hemoglobin (1:100)
FIG. 2D ICG (no dilution)
FIG. 2E Phantom Mix (1:100 dilution)
FIG. 2F ICG "Background" Fluorescence

TISSUE-LIKE PHANTOMS

CROSS-REFERENCE TO RELATED APPLICATIONS

This application claims the benefit of the filing date of U.S. Provisional Patent Application Ser. No. 60/608,200, filed on Sep. 9, 2004. The contents of this prior application are hereby incorporated by reference in their entirety.

STATEMENT AS TO FEDERALLY SPONSORED RESEARCH

This invention was made with Government support under National Cancer Institute Grant Nos. R21/33-CA-88245 and R21-CA-88870, Department of Energy Grant No. DE-FG02-01ER63188, and National Institute of Biomedical Imaging and Bioengineering Grant No. R21/R33-EB-00673. The Government thus has certain rights in the invention.

TECHNICAL FIELD

This invention relates to tissue-like phantoms, and more particularly to phantoms for use in various imaging systems, e.g., to calibrate these systems and train technicians and physicians to use these imaging systems.

BACKGROUND

Living tissue has relatively low absorbance in the near-infrared (700-1000 nm) range of the electromagnetic spectrum. Whenever photon absorbance is low, the likelihood that tissue will autofluoresce is also reduced markedly, and autofluorescence of living tissue in the NIR is minimal. Hence from an absorbance and autofluorescence standpoint, NIR light has distinct advantages. Scatter is significant at all wavelengths, although again, the absolute value of scatter tends to be lower in many tissues in the NIR.

In the last few years, there has been a dramatic rise in the use of imaging systems that exploit NIR light, and in some cases, exogenous NIR fluorophores. The three basic types of imaging systems are steady-state (e.g., continuous wave (CW)), time-domain, and frequency-domain systems. Within each system, source/detector geometry can be based on point or area illumination, and point or area detection, leading to over twelve different imaging system configurations.

Paralleling the explosion in imaging systems is a similar rise in the use of exogenous NIR fluorophores. A comprehensive review of NIR fluorophores used for in vivo imaging has been published recently (Frangioni et al., 2003). Briefly, NIR fluorescent contrast agents now exist for vascular mapping, perfusion mapping, sentinel lymph node mapping, quantitating protease activity, imaging cell injury, imaging tissue response to injury, and imaging tumors.

To develop and to test imaging systems, such as near-infrared fluorescence imaging systems, for both research and clinical use, tissue-like "phantoms" are necessary. Phantoms are non-living models of living tissue that attempt to recapitulate or mimic the optical behavior of the tissue.

Although many tissue-like phantoms have been described (see, e.g., Cubeddu et al., 1997; Wagnieres et al., 1997; Quan et al., 1993; Kelly et al., 1998; Giller et al., 2003; Boehm et al., 2001; Jiang et al., 2003), they typically have one or more of the following problems: 1) they can be difficult to construct; 2) they often have an index of refraction mismatch between a fluorescent target and the tissue-like medium; 3) they do not permit simple insertion of fluorescent objects at any depth in the phantom; 4) they do not permit a simple adjustment of background absorbance and scatter independently and with physiological relevance; 5) they cannot be constructed, tested, and then shipped to another imaging system for direct comparison; 6) they have a low stability of both fluorescent target and tissue-like material over time; 7) they lack precision in their ability to quantitate fluorescence yield of target; 8) their geometries are not suitable to both ring and planar imaging system geometries; and 9) they do not provide the ability to create isotropic and non-isotropic volumes in the same phantom.

As imaging systems and contrast agents converge, there is an increasing need for standardized NIR fluorescent phantoms that can be compared among laboratories, and that assist with the training of surgeons, and other users, on new imaging systems.

SUMMARY

The invention is based, in part, on the discovery that by combining certain components one can generate a tissue-like phantom that mimics any desired tissue, is simple and inexpensive to prepare, and is stable over many weeks or months. In addition, new multi-modal imaging objects (e.g., beads) can be inserted into the phantoms to mimic tissue pathologies, such as cancer, or merely to serve as calibration standards. These objects can be imaged using one, two, three, or more (e.g., four) different imaging modalities (e.g., x-ray computed tomography (CT), positron emission tomography (PET), single photon emission computed tomography (SPECT), and near-infrared (NIR) fluorescence) simultaneously.

The invention features tissue-like phantoms that mimic a desired tissue, e.g., a human tissue, that include (i) a viscoelastic polymer at a sufficient concentration by weight to provide sufficient strength and rigidity, e.g., to withstand manipulation; (ii) a scattering agent at a concentration such that the scattering mimics the scattering of the desired tissue; (iii) an absorbing agent at a concentration such that the absorbance, e.g., at a specific wavelength of light, mimics the absorbance of the desired tissue at the wavelength; and (iv) optionally a buffer. In specific embodiments, the viscoelastic polymer can be a gelatin, e.g., at a concentration of about 4 to 12 percent, e.g., 5, 7, 8, or 10 percent. The polymer can also be present at a sufficient concentration to provide one or more of a compression set, tear strength, tensile strength, and modulus that approximate the value in the tissue to be mimicked.

In these phantoms, the scattering agent can be a lipid composition, such as an Intralipid® (an aqueous suspension of lipid droplets), at a concentration of about 0.5 to 3.0 percent, e.g., 1.0 or 1.5 percent. The absorbing agent can be hemoglobin (e.g., human, bovine, or other animal hemoglobin) at a concentration of about 42 to 340 µM. The buffer can be Tris-buffered saline (TBS) comprising 50 mM Tris, pH 7.4 and 150 mM sodium chloride, and can include a preservative, such as sodium azide.

In certain embodiments, the new phantoms further include one or more cross-linking reagents, e.g., glutaraldehyde. The new phantoms can be designed to look and feel like human tissue.

In certain embodiments, the new phantoms further include one or more imaging objects or inclusions, such as resin beads labeled with one or more different reporter groups, e.g., Optiray® (a non-ionic contrast medium including ioversol), indocyanine green (ICG), NaF-18, and Tc-99m-methylene disphosphonate. In a particular embodiments, the inclusion is a crystal, or collection of crystals, of hydroxyapatite (HA). HA crystals, typically 100 µm in diameter, are deposited by certain malignant tumors such as breast cancer.

In another aspect, the invention includes methods of calibrating imaging systems by obtaining a new tissue-like phantom described herein having one or more known optical characteristics (e.g., scatter and absorbance); inserting the phantom into an imaging system; and imaging the phantom to calibrate the system.

The invention also includes methods of comparing two or more imaging systems by obtaining a tissue-like phantom having one or more known optical characteristics (e.g., scatter and absorbance); inserting the phantom into a first imaging system; imaging the phantom in the first system to obtain first image data; inserting the phantom into a second imaging system; imaging the phantom in the second system to obtain second image data; and comparing the first and second image data to compare the two systems.

In another aspect, the invention features methods of training a user of an imaging system by obtaining a new tissue-like phantom having one or more known optical characteristics (e.g., scatter and absorbance); inserting the phantom into an imaging system; and operating the system to image and analyze the phantom, thereby training the user. Further aspects of these methods are described in detail below.

Significant advantages of the new tissue-like phantoms include control over geometry and optical properties, compatibility with tomographic, reflectance, and other imaging systems, the ability to create both isotropic and non-isotropic phantoms, the ability to incorporate any pigmented absorbing biomolecule (e.g., hemoglobin), high stability over time, no artificial interface between volumes having different optical properties or between fluorescent targets and medium, and the representation of target fluorescence emission as "ICG equivalence."

To solve the problem of extrapolating results from one embedded fluorescent inclusion to another, and from one phantom to another, all fluorescence emissions are described herein in terms of "ICG Equivalence," that is, the measured fluorescence emission over a defined wavelength range (>795 nm), excited with NIR light of a defined wavelength and fluence rate (725-775 nm, 5 mW/cm$^2$), which is equivalent to a concentration of an ICG standard in DMSO of a defined path length (1 mm).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 4A to C are a series of images from an imaging system using the new NIR fluorescent phantoms. In these figures, ICG-loaded beads (arrows) of 1 µM ICG equivalence were placed in a non-isotropic phantom. All regions contained 50 nM ICG equivalence of background ICG and 10% gelatin in TBS. The various regions were additionally composed of: 1% Intralipid® (shown at A in FIG. 4A, and the same location in FIGS. 4B and 4C), 0.1% Intralipid® and 17 µM hemoglobin (B); 170 µM hemoglobin (C); and 1% Intralipid® and 170 µM hemoglobin (D). Beads were at a depth of 6 mm in A and 4 mm in B-D. Excitation fluence rate of 725-775 nm excitation light was 6 mW/cm$^2$. Exposure time was 250 msec.

FIGS. 5A to 5D are a series of photos or images from imaging systems of a 3.5 inch diameter tissue-like phantom. Nine 1 mm beads (arrows) with a 1 µM ICG equivalence were placed concentrically in a breast-shaped phantom. The phantom composition was 10% gelatin, 1% Intralipid®, and 17 µM hemoglobin in TBS, pH 7.4. Shown is image-guided resection of one of the (otherwise invisible) beads using a scalpel and forceps. FIG. 5C is a series of color-NIR merged images. Each series of images shows pre-surgery, resection, and post-resection images.

DETAILED DESCRIPTION

The invention is based, in part, on the discovery that by combining certain components in certain concentrations one can generate a tissue-like phantom that mimics any desired tissue in optical (and, if desired, physical) properties, is simple and inexpensive to prepare, and is stable over many weeks or months. In addition, new multi-modal imaging objects (e.g., beads) can be inserted into the phantoms to mimic tissue pathologies, such as cancer, or merely to serve as calibration standards. These objects can be imaged using one, two, or more (e.g., four) different imaging modalities simultaneously.

The new tissue-like phantoms, e.g., NIR fluorescent phantoms, have significant advantages over current models, including accurate control of geometry and optical properties of the inclusions, co-registration with other imaging systems, and quantitative evaluation of surgical technique.

Tissue-Like Phantoms

The new tissue-like phantoms mimic a desired tissue optically, and if desired physically, and are prepared from several components including (i) a viscoelastic polymer at a sufficient concentration by weight to provide satisfactory strength and rigidity to stand up to manipulation (e.g., surgical manipulation), e.g., the approximate compression set, tear strength, tensile strength, and/or modulus of tissue to be mimicked; (ii) a scattering agent at a concentration that mimics human tissue; (iii) an absorbing agent whose wavelength and concentration mimic human tissue; and (iv) optionally a buffer. The buffer is used for phantoms made of hydrogels or other polymers that require a solvent, but may not be required when the phantom is made of non-aqueous and non-solvent-based polymers. The goal is to approximate the optical characteristics, and optionally the physical characteristics (e.g., to provide a surgeon with the proper "feel" of a tissue) of the tissue to be mimicked.

Optical characteristics of many different human and animal tissues are tabulated in Cheong et al., "A Review of the Optical Properties of Biological Tissues," IEEE J. Quantum Electronics, 26:2166-85 (1990), and updated by Wai-Fung Cheong and Lihing Wang and Steven L. Jacques (Aug. 6, 1993) on the Oregon Medical Laser Center website at omlc.ogi.edu/pubs/pdf/cheong90a.pdf, the contents of both of which are incorporated by reference herein.

In the new phantoms, the polymer can be, for example, any hydrogel. Examples of different useful hydrogels, include, but are not limited to: (1) temperature dependent hydrogels that solidify or set at a certain temperature, e.g., gelatin, agarose, agar, and PLURONICS™; (2) hydrogels cross-linked by ions, e.g., sodium alginate; (3) hydrogels set by exposure to either visible or ultraviolet light, e.g., polyethylene glycol polylactic acid copolymers with acrylate end groups; and (4) hydrogels that are set or solidified upon a change in pH, e.g., TETRONICS™.

Examples of materials that can be used to form these different hydrogels include polysaccharides such as alginate, polyphosphazenes, and polyacrylates, which are cross-linked ionically, or block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

If gelatin is used, the concentration is typically between 4 and 12 percent by weight, e.g., 5, 8, or 10 percent. So-called "ballistics gel" can also be used to good effect at a concentration of about 10 percent (e.g., Kind & Knox, Type 250-A Ordnance Gelatin powder). The concentration of the polymer must be such that it enables the phantom to maintain its shape (unless the tissue to be mimicked is blood or some other liquid tissue), and in certain embodiments, to be able to withstand surgical or other manipulations. For surgical training, it is also desirable to have the phantom mimic the physical characteristics of the desired tissue. Thus, the polymer can be any material that provides adequate strength and rigidity to withstand manipulation by a surgeon or technician, and provides the physical characteristics of the tissue to be mimicked.

For example, the polymer should provide one or more of the approximate (e.g., within about 20% of the natural tissue parameters) compression set, tear strength, tensile strength, and/or modulus of the tissue to be mimicked. These physical characteristics can be measured using testing equipment and known techniques that meet American Society For Testing and Materials (ASTM) standards. First, the desired characteristics of a tissue are measured, and then these characteristics are modeled in the new tissue-like phantoms. Both the tissue and the phantom can be measured using the same equipment. To modify the physical characteristics of the phantoms, they can be for can be cross-linked for various periods of time (typically 1-2 hours) with various concentrations (typically 0.1-1%) of a cross-linking agent, e.g., glutaraldehyde, 1,8-naphthalimides, diphenylphosphorylazide (DDPA), or 1-ethyl-3,3-dimethyl-aminopropyl-carbodiimide (EDAC). This cross-linking permits fine-tuning of their mechanical properties, with more highly cross-linked phantoms remarkably similar to living tissue when cut with a scalpel. The cross-linking agents presumably cross-link both the buffer (Tris) and protein components of the phantom, and thus re-measurement of all optical properties can be performed following cross-linking. Cross-linking does not appear to affect significantly NIR fluorescence emission from inclusions.

The scattering agents can be a lipid composition, such as one of the known Intralipids®. For example, 1000 mL of Intralipid 10% contains: purified soybean oil 100 g, purified egg phospholipids 12 g, glycerol anhydrous 22 g, and water for injection q.s. ad 1000 mL. Osmolality (approx.): 300 mOsm/kg water. 1000 mL of Intralipid 20% contains: purified soybean oil 200 g, purified egg phospholipids 12 g, glycerol anhydrous 22 g, and water for injection q.s. ad 1000 mL. Osmolality (approx.): 350 mOsm/kg water. In addition, 1000 mL of Intralipid 30% contains: purified soybean oil 300 g, purified egg phospholipids 12 g, glycerol anhydrous 16.7 g, and water for injection q.s. ad 1000 mL. Osmolality (approx.): 310 mOsm/kg water.

Other scattering agents that mimic the scattering characteristics of the desired tissue can be used. If the tissue to be mimicked has little scattering, such as blood or bloody bodily fluids, then no scattering agent is added to the phantom. Otherwise, about 0.5 to 2.0 percent, e.g., 1.0 or 1.5 percent, is added to the phantom mixture.

The absorbing agent can be any material that absorbs the imaging radiation, e.g., light, near infrared light, or x-rays, to the same or similar extent as materials in the tissue to be mimicked. For example, to mimic typical muscle or fat tissue, e.g., breast tissue, hemoglobin is a useful absorbing agent. Of course, any protein, or natural or synthetic material that has the same absorption characteristics as hemoglobin can also be used. To mimic skin, melanin (or an equivalent) can be used as the absorbing agent. To mimic heart muscle, myoglobin (or an equivalent) can be used.

The absorbing agent concentration is again based on the level of absorption in the tissue to be mimicked. Generally the absorbing agent is present at a concentration of 0 to 5.0 percent, e.g., 0.5 to 1.5 percent, e.g., 1.1 percent. However, the concentration of hemoglobin needed to mimic blood is about 36 percent.

The buffer is typically a liquid that controls the pH of the phantom, largely to maintain stability. For example, the buffer can be Tris-buffered saline (TBS) composed of 50 mM Tris, pH 7.4 and 150 mM sodium chloride. The buffer will typically include a preservative, such as azide, especially if a natural polymer such as gelatin is used to prepare the phantom. The preservative should prevent the growth of bacteria, fungi, and other organisms in the phantom, and should preferably also stabilize the other agents in the phantom, such as the absorbing agent, e.g., hemoglobin. For example, sodium azide can be added (e.g., to a final concentration of 0.1 to 2.0 percent, e.g., 0.5%) to bind methemoglobin and block re-oxygenation, and to act as a preservative (TBS/azide). Other known preservatives can be used.

The tissue phantoms are prepared by mixing all of the components while the polymer or gelling agent is in liquid form, and then pouring the liquid mixture into a mold in the desired shape, e.g., in the shape of a specific tissue (e.g., a breast) or organ (e.g., a liver or heart). Thereafter, the polymer is solidified, e.g., by changing the temperature, pH, cation or anion content, irradiating the mixture (e.g., with UV light) or some other physical change.

The new tissue-like phantoms can contain imaging objects or inclusions that mimic small tumors or tissue abnormalities, such as calcifications. For example, an object of 1 μl in size mimics a tumor of approximately 1 million cells in size. An object of about 1 ml in size mimics a mass of about 1 billion cells. These inclusions can be detected using one or more imaging modalities. For example, standard calibration beads can be used. The inclusions are located in the phantoms after the phantom is solidified, or by pouring a layer of the liquid mixture into a mold, adding the inclusions, adding a second layer of the mixture to secure the inclusions, and then once the second layer has solidified, adding the remaining mixture.

The imaging objects can be in the form of polymer or resin beads, labeled with various reporter groups such as contrast agents. In some embodiments, dual-modal imaging objects, e.g., optical-radioscintigraphy, optical-MRI, or optical-CT calibration sources, are used.

In other examples, anionic exchange beads can be used to prepare single mode, dual-mode, or higher number multi-modal imaging objects. Anion exchange beads (AG1-X8, Bio-Rad, Hercules, Calif.) can be purchased as a mixture of diameters from 45 μm to 1180 μm, and sieved to a population of mean diameter ±10% using brass sieves (VWR). For example, one can use 75±7.5 μm and 1000±100 μm diameter beads, e.g., 85 to 1180 μm diameter beads. Contrast agents can be one or more of Optiray® (for CT), indocyanine green (ICG) (for NIR), NaF-18 (for PET), and Tc-99 m-methylene disphosphonate (for SPECT). These objects can then be imaged with the eXplore Locus MicroCT® (GE Healthcare, Waukesha, Wis.) for CT; any NIR fluorescence system for NIR; the Discovery® LS (GE Healthcare, Waukesha, Wis.) for PET, and the Custom Park Isocam® (Isocam Technologies) for SPECT. Any known reporter groups, e.g., contrast agents, that can be linked, e.g., covalently or non-covalently, to the imaging objects, e.g., beads, can be used.

Optiray® is an injectable low osmolar, nonionic, contrast media agent intended for intravascular administration. Optiray® 350 is intended to be therapeutically and biologically inert when injected into the body for use in organ or tissue enhancement in CT, X-Ray, and fluoroscopy imaging procedures. Each milliliter of Optiray® 350 contains 741 mg of ioversol, 3.6 mg of tromethamine as a buffer, and 0.2 mg of edetate calcium disodium as a stabilizer.

In specific embodiments, for CT/NIR, the beads can be loaded with 88 mM Optiray® and 10 μM of ICG and incubated at room temperature for 20 minutes with end-over-end rotisserie turning. For SPECT/CT, the beads can be labeled with 5 mCi of Tc-99 m and 2 μM of ICG for fifteen minutes at room resulting in 10 μCi Tc-99 m per bead and an ICG equivalence of 500 nM (i.e., the equivalent fluorescence as 500 nM ICG in DMSO. For PET/NIR, the beads can be labeled with 5 mCi of F-18 and 2 μM of ICG for fifteen minutes at room temperature resulting in 5 μCi F-18 per bead and ICG equivalence of 500 nM.

Optimal labeling methods can be easily determined for CT/NIR, SPECT/NIR, PET/NIR, and other imaging combinations. For example, new CT/NIR imaging objects made as beads labeled with 88 mM of Optiray® and 10 μM of ICG resulted in signal to background ratios of >10:1 and >25:1 for CT and NIR, respectively.

The new multi-modal, sub-millimeter objects can be imaged with CT, PET, SPECT, near-infrared fluorescence, and/or other modalities simultaneously. These beads have the capability of being used as fiducials for registration of data sets from multiple modalities. For example, functional data from PET, SPECT, or NIR, can be registered with anatomical data from CT. Multi-modality sources may also be used as calibration phantoms for a breadth of imaging systems.

Methods of Use

For researchers the new tissue-like phantoms can be used as standardized calibration phantoms to compare performance among different imaging systems in terms of sensitivity, reconstruction algorithms, and other system features.

For commercial companies, the new tissue-like phantoms provide a valuable standardization tool to compare performance of any one imaging system against another type of system. The new phantoms are also quite valuable as training tools for simulations of operation of the system under real conditions. For example, rather than having a technician practice using a new imaging system (e.g., for imaging breast tissue) on living patients, often at considerable discomfort to the patient, technicians can use the new tissue-like phantoms.

For surgeons, the new tissue-like phantoms permit surgeons to "operate" (physically cut and dissect) on them to learn the functions of the imaging system and to become proficient in using, e.g., the NIR fluorescence imaging and pseudo-colored overlay of a given system to find target tumors and perform surgery (e.g., removal of a tumor mass). Again, this is far better and cheaper training for the surgeon than to use an animal, human cadaver, or living patient for training purposes. Anything that decreases the learning curve for surgeons will ultimately save thousands of dollars and decrease risk to patients.

EXAMPLES

The following examples are illustrative and are not meant to be limiting.

Example 1

Preparing NIR Fluorescence Imaging System Tissue-Like Phantoms

We prepared various tissue-like phantoms. In each case, the bulk phantom material was composed of gelatin, Intralipid®, and hemoglobin, in varying concentrations. The scattering and absorbing properties of these materials were measured using the inverse adding-doubling method from 670-830 nm. NIR fluorescent inclusions were made using indocyanine green (ICG)-labeled polystyrene divinylbenzene beads or Pam78-labeled hydroxyapatite crystals, similar to those found in breast cancer. The moles of fluorophore per inclusion were measured precisely, and expressed as "equivalence" to ICG in DMSO (as described in further detail below).

We used the following reagents: NF-grade gelatin (catalog #EM-GX0048-1) from VWR (West Chester, Pa.); sterile Intralipid® (20%) purchased from Baxter (Deerfield, Ill.); bovine hemoglobin and indocyanine green (ICG) from Sigma (St. Louis, Mo.); AG 1-X8 anion exchange resin (catalog #140-1422) from Bio-Rad (Hercules, Calif.); Pam78 prepared as described (Zaheer et al., 2001); and hydroxyapatite (HA) crystals (catalog #391947) from Calbiochem (La Jolla, Calif.).

We constructed the phantom as follows. The buffer for all phantoms was Tris-buffered saline (TBS) composed of 50 mM Tris, pH 7.4 and 150 mM sodium chloride. Sodium azide was added to a final concentration of 0.5% to bind methemoglobin and block re-oxygenation, and to act as a preservative (TBS/azide). Gelatin was suspended at the desired concentration (e.g., 4, 6, 8, or 10%) in TBS (GTS), and warmed with stirring to 25° C. until completely dissolved. Solidification of the GTS mixture should be done as rapidly as possible to avoid the separation of the Intralipid® (which is present in 0.5, 1, 2, or 3%). Hemoglobin was added at concentrations of 42, 85, 170, or 340 µM. ICG was added at concentrations of 125, 250, 500, and 1000 nM. Specific percentages for individual phantoms, and their test results, are described in the examples below.

The NIR fluorescent target inclusions were produced as follows. Beads were sieved to a diameter of 1000±100 µm using a 20 mesh (850 µm square holes) brass sieve (VWR catalog #57334-112). For bead loading, ICG was diluted in TBS to 2× and mixed 1:1 with a 50% bead slurry, vortexed for 3 seconds, incubated 20 minutes, and washed 4× with TBS. Pam78 was loaded onto HA in a similar fashion.

Similar to sub-millimeter radioscintigraphic calibration sources previously published by our group (English et al., 2002), the particular resin used in this study is available in wet bead diameters from 45 µm to 1180 µm, which can be sieved to any desired size, and is also available with crosslinking ranging from 2% to 8%. The latter value is important, since it determines the exclusion limit of the bead interior. The 8% bead used in this study does not exclude 775 MW ICG, resulting in relatively homogeneous fluorescence over the volume of the bead.

A second NIR fluorescent target used in this study was hydroxyapatite (HA) crystals loaded with Pam78, a NIR fluorescent derivative of the bisphosphonate pamidronate (Zaheer et al., 2001). Pam78 has been used previously for in vivo imaging of sites of osteoblastic activity and the simulated calcification of breast cancer. Pam78-loaded HA is an ideal fluorescent target for tissue-like phantoms since it has biologic and medical relevance (discussed below), and can be loaded with physiologically relevant concentrations of fluorophore.

Figure 1A:
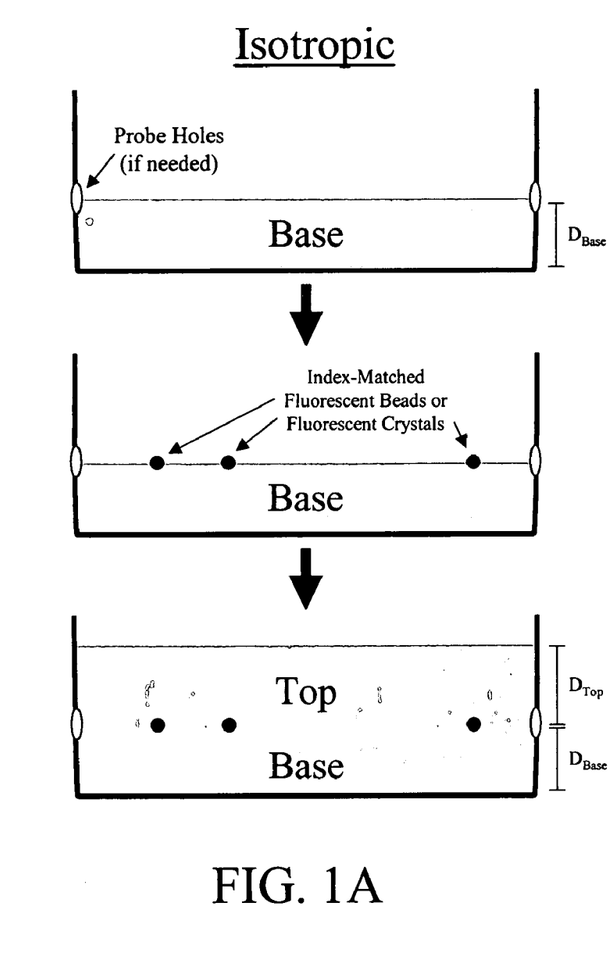
FIGS. 1A and B are schematic diagrams of methods of construction of tissue-like phantoms, e.g., for NIR fluorescence imaging. By choosing the scatter, absorbance, and background fluorescence of the base and top, isotropic (FIG. 1A) or non-isotropic (FIG. 1B) phantoms can be created.
Figure 1B:
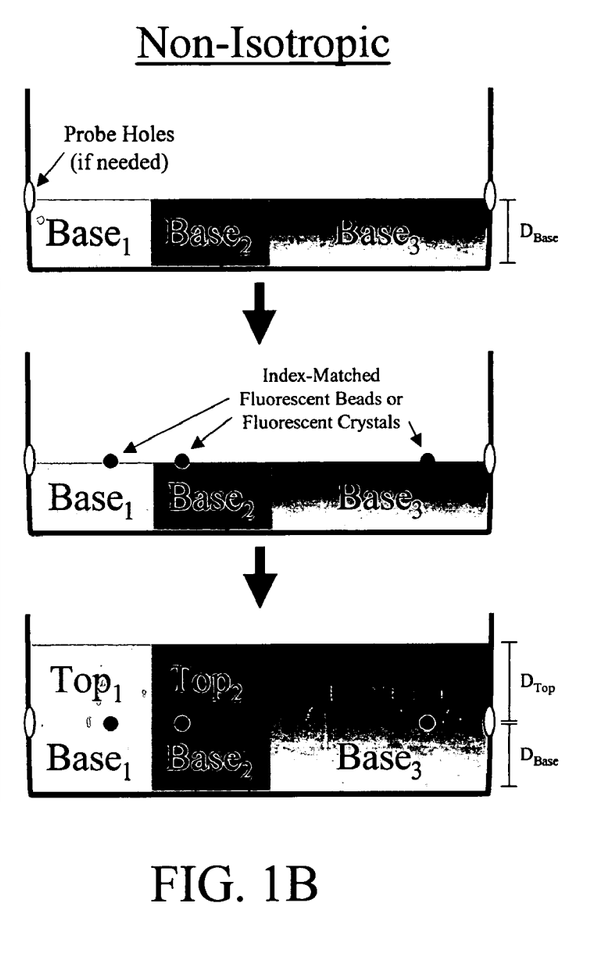

Phantoms were prepared in covered plastic food storage containers of the desired size and geometry (FIGS. 1A and 1B). By choosing the scatter, absorbance, and background fluorescence of the base and top, isotropic (FIG. 1A) or non-isotropic (FIG. 1B) phantoms can be created. In non-isotropic phantoms, optical properties can be varied in three dimensions, including the use of gradients (e.g., Base3/Top3). For tomography, probe holes are pre-drilled and taped over before filling, or the container is coated with vegetable oil for easy removal of the entire phantom.

Fluorescent targets can be placed at any position in 3-space within the phantom. As shown in FIG. 1A the inclusions were inserted into the phantoms by pouring a first layer of the liquid gelatin mixture into the mold (to a depth of $D_{Base}$), allowing this layer to solidify, adding the inclusions, and then adding a second layer of the gelatin mixture (to a depth of $D_{Top}$). FIG. 1B shows schematically how to prepare a non-isotopic phantom with 3 different base layer portions and three top layer portions.

Example 2

Testing of Phantoms

Optical measurements were made on the new phantoms as follows. Absorbance and fluorescence measurements were performed on an Ocean Optics™ (Dunedin, Fla.) spectrometer using a 1 cm quartz cuvette (Starna Cells, Atascadero, Calif.). Intraoperative NIR fluorescence imaging was performed as described in detail previously (De Grand et al., 2003).

Phantom absorbance, scatter, and background fluorescence were varied from $\mu a=0$ to $0.093$ $mm^{-1}$ at 780 nm, $\mu s'=0$ to $2.06$ $mm^{-1}$, and 0 to $2.5$ $\mu M$ ICG equivalence, respectively, by changing the composition of the phantom. Even various regions of the same phantom could have different properties, without refractive interfaces. Fluorescent inclusions, having ICG equivalence from 0 to 5 µM, were varied in size from 75 to 1000 µm. 3-D positioning of fluorescent inclusions was verified independently using a GE Locus® small animal CT system to within +/−90 µm. Therefore, extremely complex phantoms, having any desired optical properties and geometries can be constructed, inexpensively and easily, using this system.

Figure 2A:
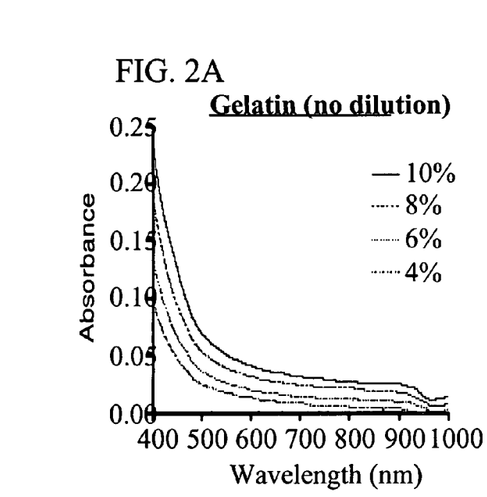
FIGS. 2A-F are a series of graphs that characterize phantom components. The figures show absorbance as a function of wavelength for the various phantom medium components (FIG. 2A—Gelatin in TBS/azide (GTS); 2B—Intralipid in 10% GTS; 2C—Bovine hemoglobin in 10% GTS; 2D—ICG in 10% GTS; 2E—Mixture of 2A-C; and 2F—ICG "background" fluorescence added to the phantom from 2E).
Figure 2B:
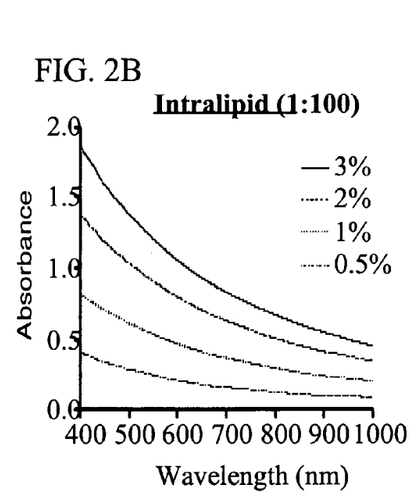
Figure 2C:
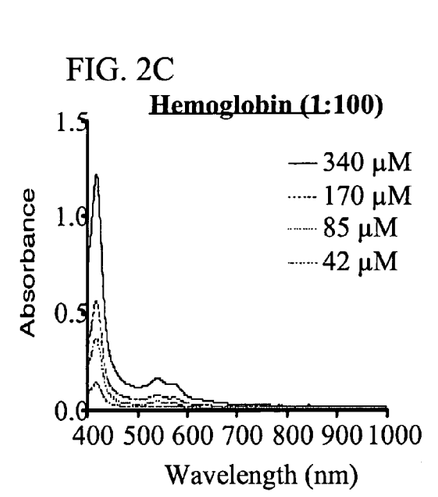
Figure 2D:
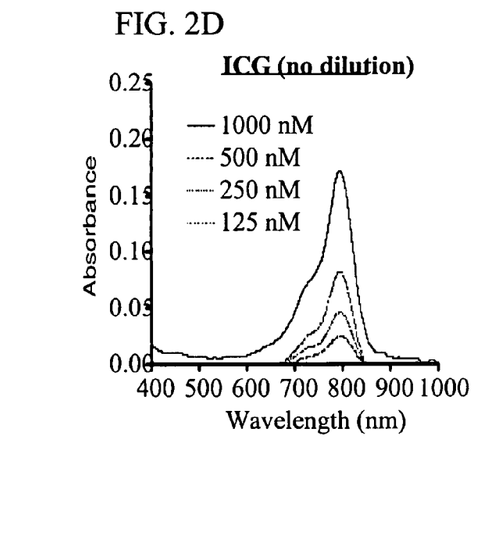
Figure 2E:
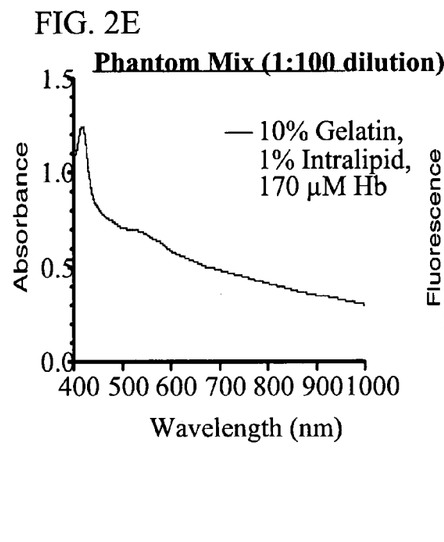
Figure 2F:
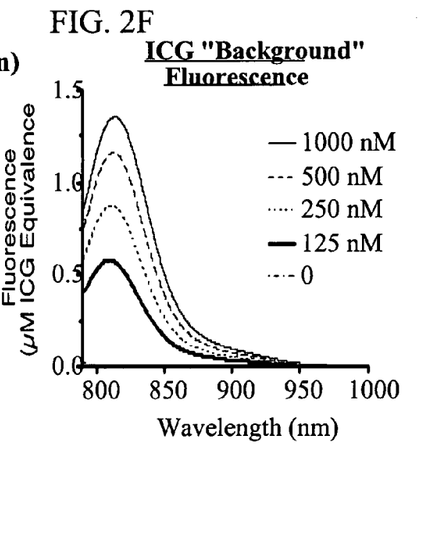

Absorbance of the medium was controlled by the concentration of oxy- and deoxyhemoglobin (the ratio of which is adjusted using azide) (see FIG. 2C, which shows Bovine hemoglobin in 10% gelatin in TBS/azide (GTS)) and/or other biomolecules. In particular, FIG. 2A shows the effect of gelatin concentration (GTS) on absorbance. FIG. 2B shows the effect of Intralipid® concentration in 10% GTS on absorbance. FIG. 2C shows the effect of hemoglobin concentration in 10% GTS on absorbance. FIG. 2D shows the effect of ICG concentration in 10% GTS on absorbance. FIG. 2E shows the absorbance pattern for a specific phantom (10% gelatin, 1% Intralipid®, and 170 µM hemoglobin). FIG. 2F shows the effect of ICG concentration on background fluorescence when added to the phantom of FIG. 2E.

Scatter was controlled by the concentration of Intralipid®, with a small contribution from the gelatin at high concentrations. The absorbance, scatter, and background fluorescence of the phantom can be varied in three dimensions, hence, extremely complex phantoms having any desired optical properties and geometry can be constructed inexpensively and easily using this system.

Figure 2G:
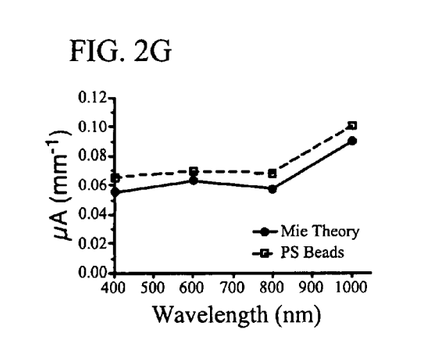
FIGS. 2G-O are a series of graphs that characterize phantom optical properties the figures show µA (2G, 2J, 2M), µs' (2H, 2K, 2N), and anisotropy (2I, 2L, 2O) as a function of wavelength for polystyrene beads (2G-I), various concentrations of Intralipid® (2J-L), or whole phantoms (2M-O).
Figure 2H:
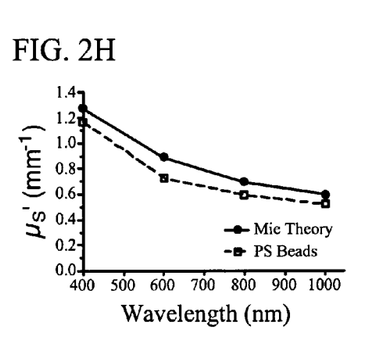
Figure 2I:
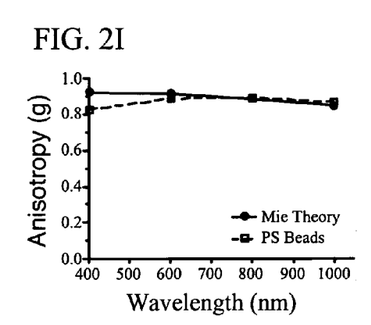
Figure 2J:
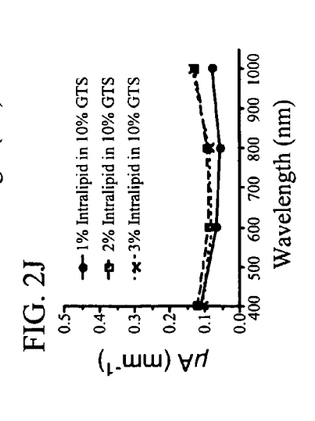
Figure 2K:
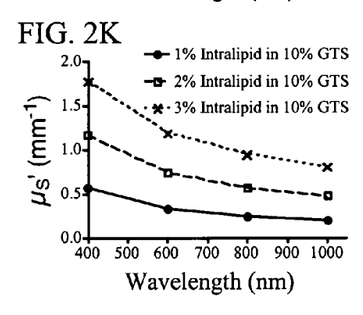
Figure 2L:
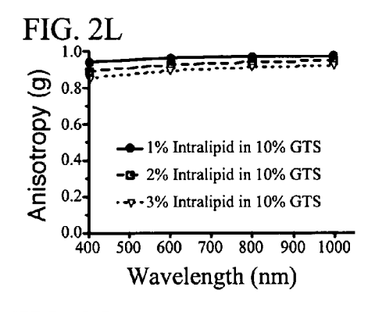

Optical properties of the phantoms were measured on a Lambda 19 (Perkin Elmer, Boston, Mass.) UV/Vis/NIR spectrophotemeter equipped with a 150 mm integrating sphere. The scattering and absorbing properties of samples were computed using the inverse adding-doubling method from 400-1000 nm (Prahl et al., 1993; the algorithm is available for download at omlc.ogi.edu/software/iad/). Validation of the inverse adding-doubling algorithm employed was performed by comparing results of Mie scattering theory with calibrated polystyrene beads of defined optical properties (Ma et al., 2003). As shown in FIGS. 2G-2I, theoretical and empirical values for $\mu A$, $\mu_s'$, and anisotropy were closely correlated over the wavelength range 400-1000 nm. Optical properties of the various phantom components detected over this wavelength range are shown in FIGS.

Figure 2M:
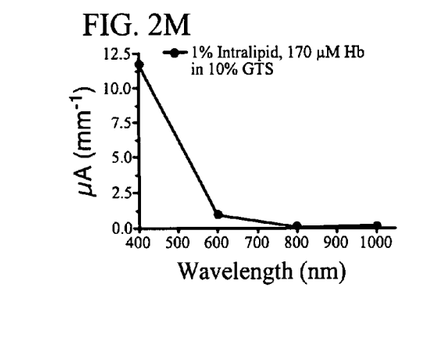
Figure 2N:
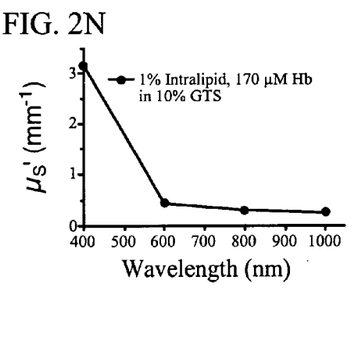
Figure 2O:
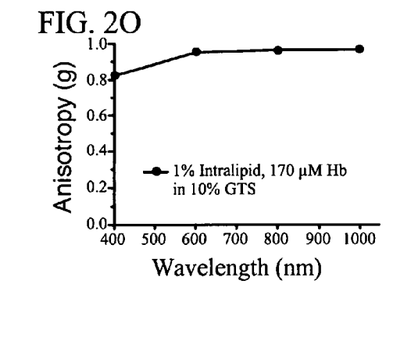

2J-2L (various concentrations of intralipid in 10% GTS) and FIGS. 2M-2O (complete phantom).

The NIR fluorescent targets were characterized as follows. To solve the problem of extrapolating results from one embedded fluorescent inclusion to another, and from one phantom to another, we report all fluorescence emissions in terms of "ICG Equivalence," that is, the measured fluorescence emission over a defined wavelength range (>795 nm), excited with NIR light of a defined wavelength and fluence rate (725-775 nm, 5 mW/cm$^2$), which is equivalent to a concentration of an ICG standard in DMSO of a defined path length (1 mm). DMSO is one of the few solvents in which ICG is stable, and for which an absolute quantum yield (13%) has been reported. Hence, by expressing embedded target fluorescence as ICG equivalence, the performance of virtually any other NIR fluorophore can be extrapolated. Note the quenching of ICG at high loading concentration (FIG. 3B).

Figure 3A:
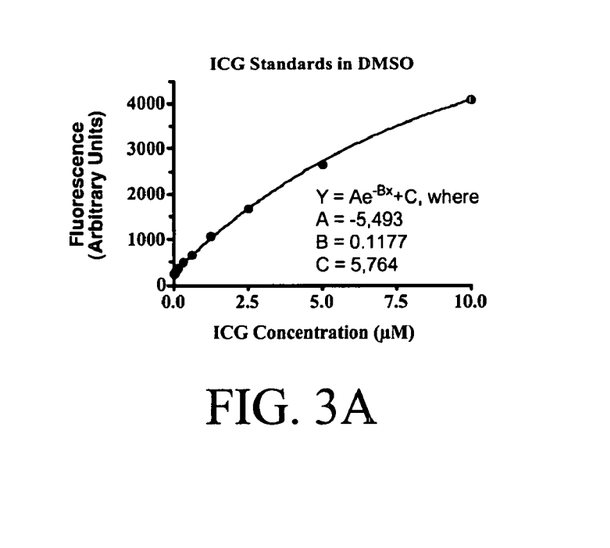
FIGS. 3A-D are a series of graphs and photomicrographs that characterize NIR fluorescent targets (FIG. 3A—0.79 µL ICG standards in DMSO; 3B—ICG equivalence of individual 1 mm (0.79 µL) ICG-loaded anion exchange beads expressed as a function of loading concentration; 3C—100 µm (height) ICG standards in DMSO; and 3D—Pam78-labeled HA crystals with a 1 µM ICG equivalence.
Figure 3B:
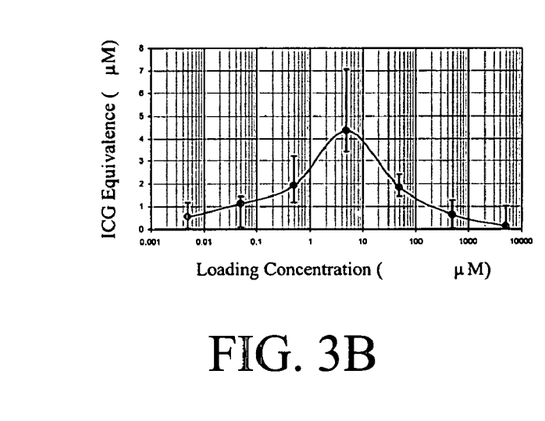
Figure 3C:
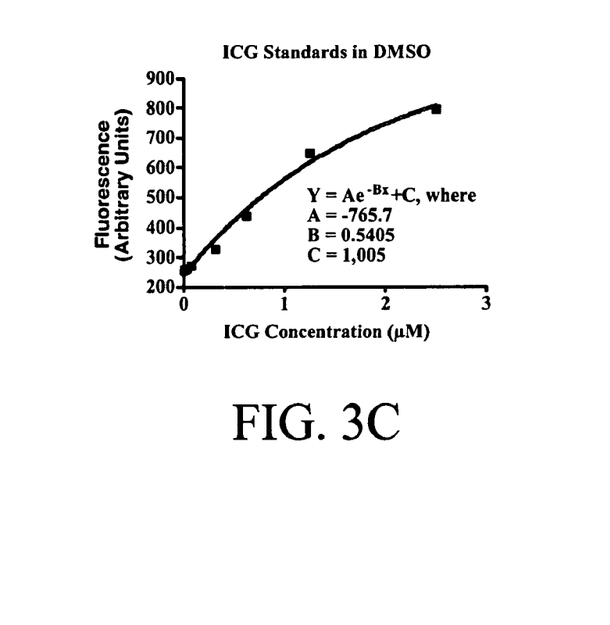
Figure 3D:
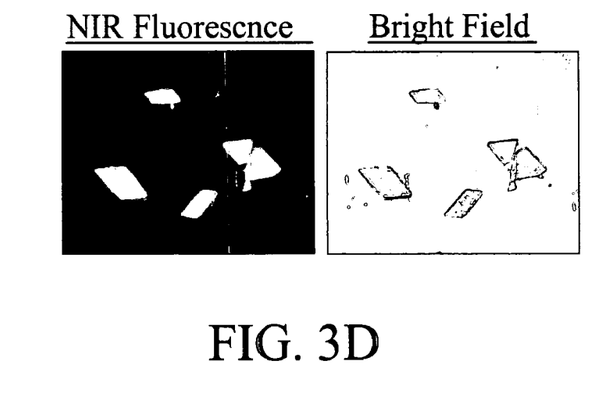

FIGS. 3A-C are a series of graphs that characterize the NIR fluorescent targets. FIG. 3A shows 0.79 µL ICG standards in DMSO. FIG. 3B shows ICG equivalence of individual 1 mm (0.79 µL) ICG-loaded anion exchange beads expressed as a function of loading concentration. FIG. 3C shows 100 µm (height) ICG standards in DMSO. FIG. 3D shows images of Pam78-labeled HA crystals with a 1 µM ICG equivalence under both NIR fluorescence and bright field illumination.

The fluorescent targets described in this study were chosen for their relevance to important medical applications. For tumor cell receptor imaging, an abundant receptor will be present at 100,000 to 600,000 copies on the cell surface. Assuming a cell volume of 1 pL, and no endocytosis, the maximum concentration of contrast agent achievable is 160 nm to 1 µM. As demonstrated in FIGS. 3A to 3C, the anion exchange beads using in this study can be loaded with an ICG equivalence throughout this physiologic range. The beads are also available in volumes ranging from 45 pL to 820 nL, corresponding to roughly 45 to 820,000 cells. Pam78-loaded HA also has significant biologic relevance in light of recent reports that the malignant calcification of breast cancer is composed of HA, and typically not other calcium salts.

Phantom homogeneity was tested by taking 20 full spectrum (400-1000 nm) reflectance measurements each in the X and Y directions, at 5 mm intervals. Variation over this 10 cm distance, in either direction, was less than 2%.

The stability of the phantom over time was measured at 400 nm, 600 nm, 800 nm, and 1000 nm over a 4-week period. At wavelegnths from 600-1000 nm, there was virtually no change in optical properties of the phantom components. However, at 400 nm and starting at approximately 2 weeks, there was evidence of Hb transition from the oxy-, deoxy- and possibly met-Hb states, as well as evidence of diffusion of Hb within the phantom. Although these results should have no impact on NIR fluorescence experiments, use of multi-compartment phantoms for measuring Hb concentration over periods greater than 2 weeks can be performed with these results in mind.

Example 3

Imaging System Calibration and Performance Assessment

Figure 4A:
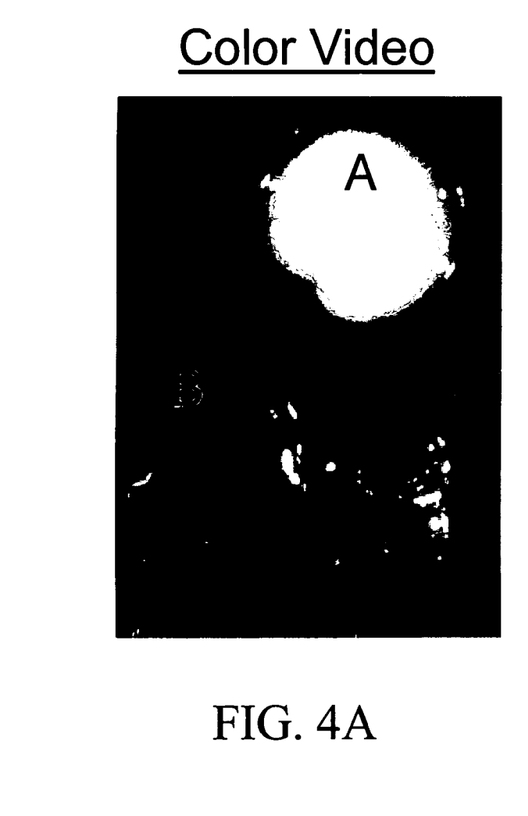
FIG. 4A is a color video (rendered in black and white here)
Figure 4B:
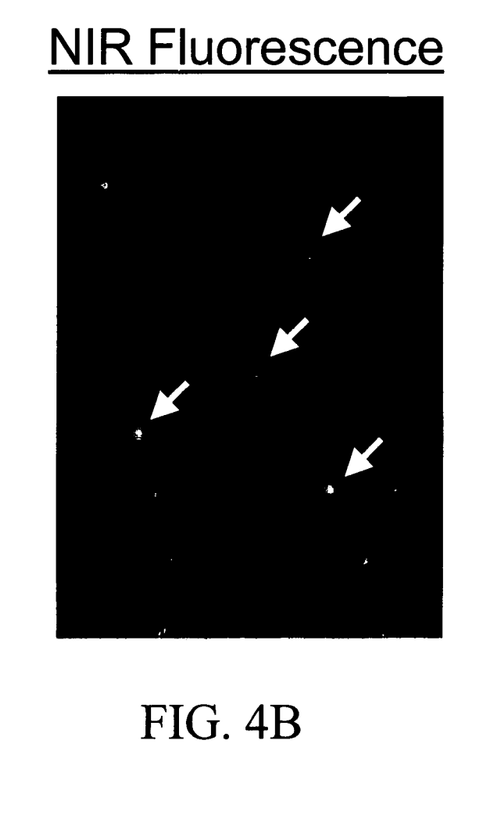
FIG. 4B is a NIR fluorescence image.
Figure 4C:
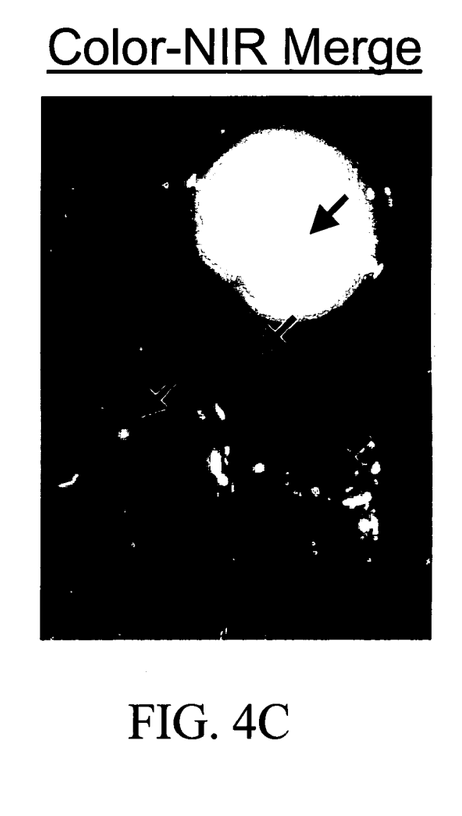
FIG. 4C is a merged image of both color and NIR.

One of the major uses for these phantoms is in assessing the performance of tomographic and reflectance imaging systems. This feature is illustrated in FIGS. 4A to 4C for a NIR fluorescence imaging system designed for large animal and human studies. The non-isotropic phantom is particularly relevant to in vivo conditions where different tissue planes generate gradients of optical properties. The SBR (signal-to-background ratio), as well as visual discrimination of the targets, could be measured as a function of fluence rate, system optics, and camera integration time. Given its stability (data not shown), such a phantom could theoretically be shipped to any other laboratory for calibration or comparative assessment of different systems. The phantoms can be stored under refrigeration, e.g., at 4° C., for weeks or months.

In particular, FIGS. 4A to 4C are a series of images from an imaging system using the new NIR fluorescent phantoms. In these figures, ICG-loaded beads (arrows) of 1 µM ICG equivalence were placed in a non-isotropic phantom. All regions contained 50 nM ICG equivalence of background ICG and 10% gelatin in TBS. The various regions were additionally composed of: 1% Intralipid® (shown at A in FIG. 4A, and the same location in FIGS. 4B and 4C), 0.1% Intralipid® and 17 µM hemoglobin (B); 170 µM hemoglobin (C); and 1% Intralipid® and 170 µM hemoglobin (D). Beads were at a depth of 6 mm in A and 4 mm in B-D. Excitation fluence rate of 725-775 nm excitation light was 6 mW/cm$^2$. Exposure time was 250 msec.

FIG. 4A is a color video (rendered in black and white here), FIG. 4B is a NIR fluorescence image, and FIG. 4C is a merged image of both color and NIR. Based on these results, the new phantoms can be used to assess the performance of tomographic and reflectance imaging systems.

Example 4

Training in Imaging System Operation and Image-Guided Surgery Using NIR Fluorescent Phantoms The use of NIR fluorescent phantoms for surgical training is shown in FIGS. 5A-5D. The phantom provides a means to train the surgeon on system software (not shown), image-guided dissection, image-guided resection, and post-resection inspection of the surgical field. Given the close index matching between fluorescent targets and phantom, it is virtually impossible to find the target without NIR image guidance, thus providing a stringent standardization for assessing surgical technique.

Figure 5A:
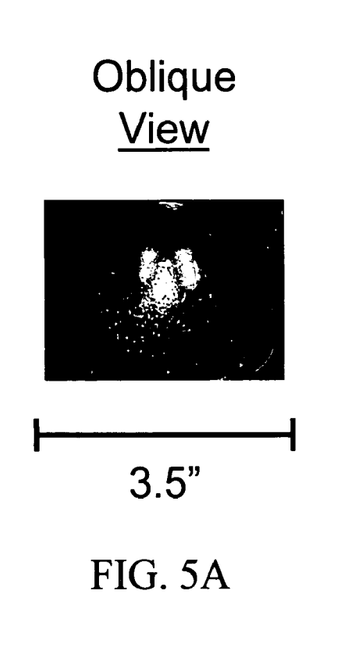
FIG. 5A is a photo of an oblique view.
Figure 5B:
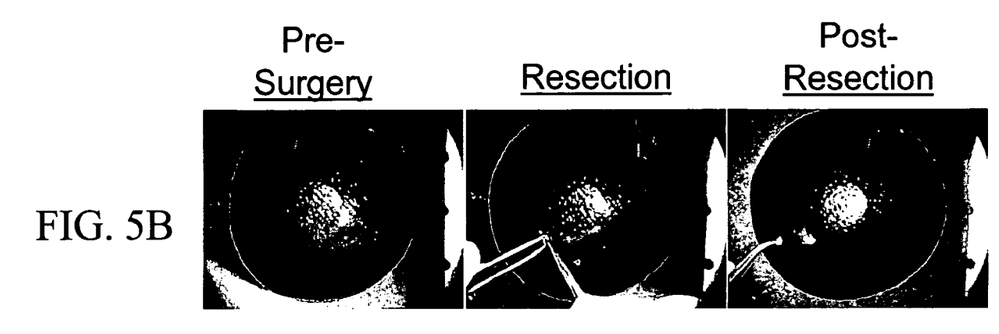
FIG. 5B is a series of color video images (shown here in black and white)
Figure 5C:
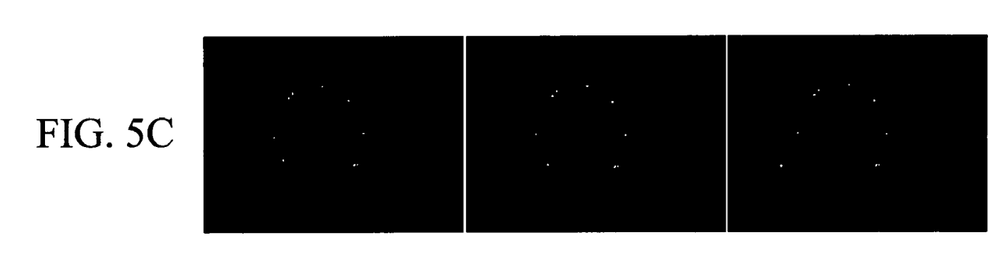
FIG. 5C is a series of NIR fluorescence images.
Figure 5D:
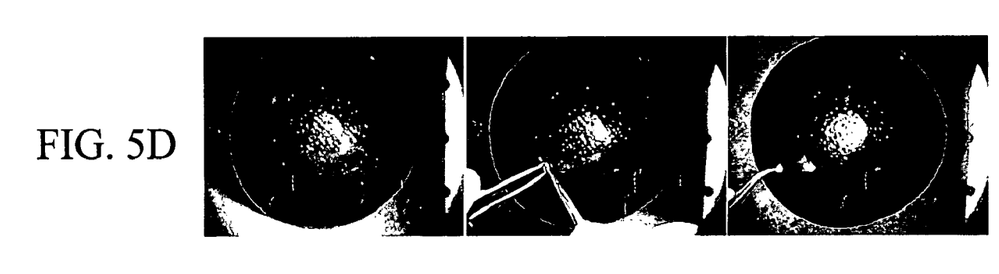

In particular, FIGS. 5A to 5D are a series of photos or images from imaging systems of a 3.5 inch diameter tissue-like phantom. Nine 1 mm beads (each approximating a collection of 7.9×10$^5$ cells; arrows) with a 1 µM ICG equivalence were placed concentrically in a breast-shaped phantom (see oblique view). The phantom composition was 10% gelatin, 1% Intralipid®, and 17 µM hemoglobin in TBS, pH 7.4. Shown is image-guided resection of one of the (otherwise invisible) beads using a scalpel and forceps. FIG. 5A is a photo of an oblique view; FIG. 5B is a series of color video images (shown here in black and white); FIG. 5C is a series of NIR fluorescence images; and FIG. 5C is a series of color-NIR merged images. Each series of images shows pre-surgery, resection, and post-resection images.

The translation of intraoperative NIR fluorescence technology to the clinic will require the training of medical technologists (e.g., for tomographic breast imaging) and surgeons (e.g., for intraoperative reflectance imaging systems). Such training will be greatly facilitated by the tissue-like phantoms described in this study. Such training systems that do not require animal or human contact during the steepest phase of the learning curve should find an immediate use as optical imaging reaches the clinic.

Example 5

Autofluorescence of Living Tissue

Living tissue has a low, but measurable, autofluorescence, which can be taken into account when constructing a phantom designed to mimic a particular tissue or organ. Autofluorescence of various tissues and organs was measured in pigs.

Animal protocols were in accordance with Institutional Animal Care and Use Committee Guidelines. Thirty-five kg adult male Yorkshire pigs (n=3) were purchased from E.M. Parsons and Sons (Hadley, Mass.). All animals acclimated to the animal facility for at least 48 hours prior to experimentation. Pig anesthesia was induced with 4.4 mg/kg intramuscular Telazol™ (Fort Dodge Labs, Fort Dodge, Iowa) and anesthesia maintained through a 7 mm endotracheal tube with 1.5% isoflurane/98.5% $O_2$ at 5 L/minute.

Tissues and organs were surgically exposed, then imaged using NIR excitation light of 725-775 nm, with an excitation fluence rate of 5 mW/cm$^2$ (as measured with a calibrated Orion-TH digital light power meter equipped with an Orion model 2A-SH thermopile detector head). In each field of view, and on non-absorbing and non-reflecting black matte paper (Canson Mi-Teintes, Stygian Black #425), were placed 1 mm path length ICG standards in DMSO of 0, 31, 63, 125, 250, 500, 1000, and 2000 nM, and calibration curves were created for camera exposure times of 10, 34, 67, 134, 500 and 1000 msec. From these six curves, the average the autofluorescence of the tissue or organ under study was calculated, and expressed as ICG Equivalence.

After each study, anesthetized animals are euthanized by rapid intravenous injection of 10 ml of Fatal-Plus™ (Vortech Pharmaceuticals, Dearborn, Mich.). This method of euthanasia is consistent with the recommendations of the Panel on Euthanasia of the American Veterinary Medical Association.

Table 1 shows the autofluorescence of the tissues and organs examined, expressed as ICG Equivalence using 725-775 nm excitation light at 5 mW/cm$^2$, a >790 nm long pass emission filter and a 1 mm path length of DMSO standards. Since fluorescence emission often scales non-linearly with inclusion size, it is best to match the inclusion size to the typical tumor size of the model system employed. The values in Table 1 can be used to add the appropriate level of phantom background fluorescence for the tissue type under study. This is especially useful since the relative autofluorescence of different tissues varies by over nine-fold.

TABLE 1

NIR Autofluorescence of Living Tissue

| Tissue or Organ | ICG Equivalence (nM) | Standard Deviation |
| --- | --- | --- |
| Bladder | 52.50 | 4.72 |
| Bone | 129.3 | 10.6 |
| Brain (w/o dura) | 135.5 | 13.6 |
| Brain (with dura) | 84.17 | 39.3 |
| Colon | 76.56 | 4.83 |
| Esophagus | 98.73 | 26.9 |
| Gallbladder | 35.35 | 4.30 |
| Heart | 39.53 | 19.0 |
| Kidney | 49.15 | 7.67 |
| Liver | 24.68 | 7.64 |
| Lung | 43.30 | 20.2 |
| Muscle | 48.53 | 8.79 |
| Pancreas | 55.64 | 15.7 |
| Periosteum | 179.7 | 22.0 |
| Skin (w/o hair) | 60.03 | 13.1 |
| Skin (with hair) | 166.3 | 19.8 |
| Small Intestine | 26.98 | 6.29 |
| Spleen | 15.58 | 12.4 |
| Stomach | 28.87 | 8.09 |
| Tongue | 73.84 | 19.8 |
| Trachea | 80.53 | 10.2 |

REFERENCES CITED

Frangioni, J. V., "In vivo near-infrared fluorescence imaging," Curr. Opin. Chem. Biol., 7:626-634 (2003).

Cubeddu et al., "A solid tissue phantom for photon migration studies," Phys. Med. Biol., 42:1971-9 (1997).

Wagnieres et al., "An optical phantom with tissue-like properties in the visible for use in PDT and fluorescence spectroscopy," Phys. Med. Biol., 42:1415-26 (1997).

Quan et al., "Glucose determination by a pulsed photoacoustic technique: an experimental study using a gelatin-based tissue phantom," Phys. Med. Biol., 38:1911-22 (1993).

Kelly et al., "Optical CT reconstruction of 3D dose distributions using the ferrous-benzoic-xylenol (FBX) gel dosimeter," Med. Phys., 25:1741-50 (1998).

Giller et al., "Validation of a near-infrared probe for detection of thin intracranial white matter structures," J. Neurosurg., 98:1299-306 (2003).

Boehm et al., "Contrast-enhanced near-infrared laser mammography with a prototype breast scanner: feasibility study with tissue phantoms and preliminary results of imaging experimental tumors," Invest. Radiol., 36:573-81 (2001).

Jiang et al., "Quantitative analysis of near-infrared tomography: sensitivity to the tissue-simulating precalibration phantom," J. Biomed. Opt., 8: 308-15 (2003).

Zaheer et al., "In vivo near-infrared fluorescence imaging of osteoblastic activity," Nat. Biotechnol., 19: 1148-1154 (2001).

English et al., "Sub-millimeter technetium-99 m calibration sources," Mol. Imag. Biol., 4: 380-384 (2002).

De Grand et al., "An operational near-infrared fluorescence imaging system prototype for large animal surgery," Technol. Cancer Res. Treat., 2:553-562 (2003).

Prahl et al., "Determining the optical properties of turbid media by using the adding-doubling method," Appl. Opt., 32: 559-568 (1993).

Ma et al., "Determination of complex refractive index of polystyrene microspheres from 370 to 1610 nm," Phys. Med. Biol., 48: 4165-72 (2003).

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A tissue-like phantom that mimics a desired tissue comprising
   a viscoelastic polymer at a sufficient concentration by weight to provide sufficient strength and rigidity to withstand manipulation;
   a scattering agent at a concentration such that the scattering of the phantom mimics the scattering of the desired tissue;
   an absorbing agent at a concentration such that the absorbance at a specific wavelength mimics the absorbance of the desired tissue; and
   optionally a buffer.

2. The phantom of claim 1, wherein the viscoelastic polymer is gelatin at a concentration of about 4 to 12 percent.

3. The phantom of claim 1, wherein the viscoelastic polymer is present at a sufficient concentration to provide one or more of a compression set, tear strength, tensile strength, and modulus of the tissue to be mimicked.

4. The phantom of claim 1, wherein the scattering agent is a lipid composition at a concentration of about 0.5 to 3.0 percent.

5. The phantom of claim 4, wherein the lipid composition is an aqueous suspension of lipid droplets at a concentration of about 0.5 to 3.0 percent.

6. The phantom of claim 1, wherein the absorbing agent is hemoglobin at a concentration of about 42 to 340 μM.

7. The phantom of claim 1, wherein the buffer is Tris-buffered saline (TBS) comprising 50 mM Tris, pH 7.4 and 150 mM sodium chloride.

8. The phantom of claim 1, wherein the buffer comprises a preservative.

9. The phantom of claim 7, wherein the preservative is sodium azide.

10. The phantom of claim 1, further comprising one or more imaging objects.

11. The phantom of claim 10, wherein the one or more imaging objects are resin beads labeled with one or more different reporter groups.

12. The phantom of claim 11, wherein the one or more different reporter groups are any one or more of a non-ionic contrast medium including ioversol, indocyanine green (ICG), NaF-18, and Tc-99m-methylene disphosphonate.

13. A method of calibrating an imaging system, the method comprising
   obtaining a tissue-like phantom of claim 1 having one or more known optical characteristics;
   inserting the phantom into an imaging system; and
   imaging the phantom to calibrate the system.

14. A method of comparing two or more imaging systems, the method comprising
   obtaining a tissue-like phantom of claim 1 having one or more known optical characteristics;
   inserting the phantom into a first imaging system;
   imaging the phantom in the first system to obtain first image data;
   inserting the phantom into a second imaging system;
   imaging the phantom in the second system to obtain second image data; and
   comparing the first and second image data to compare the two systems.

15. A method of training a user of an imaging system, the method comprising
   obtaining a tissue-like phantom of claim 1 having one or more known optical characteristics;
   inserting the phantom into an imaging system;
   operating the system to image and analyze the phantom, thereby training the user.

16. The method of claim 15, wherein the phantom contains an imaging object mimicking a tumor mass or other disease pathology, and the user is a surgeon.

17. A method of making a tissue-like phantom, the method comprising
   mixing (i) a viscoelastic polymer at a sufficient concentration by weight to provide sufficient strength and rigidity to withstand manipulation; (ii) a scattering agent at a concentration of 0 to about 4 percent; (iii) an absorbing agent at a concentration of 0 to about 36 percent; and (iv) optionally a buffer to form a liquid mixture;
   pouring the liquid mixture into a mold having a desired geometry; and
   providing conditions that enable the liquid mixture to solidify.

18. The method of claim 17, further comprising inserting imaging objects into the phantom.

19. The phantom of claim 1, wherein the wavelength is about 780 nm.

* * * * *